United States Patent
Panmai et al.

(10) Patent No.: US 10,842,751 B2
(45) Date of Patent: *Nov. 24, 2020

(54) PHARMACEUTICAL COMPOSITIONS CONTAINING DORAVIRINE, TENOFOVIR DISOPROXIL FUMARATE AND LAMIVUDINE

(71) Applicant: Merck Sharp & Dohme Corp., Rahway, NJ (US)

(72) Inventors: Santipharp Panmai, Cranford, NJ (US); Aditya Tatavarti, Chalfont, PA (US); Andrew M. Farrington, Collegeville, PA (US); Varsha Biyyala, Somerset, NJ (US); Leonardo R. Allain, Lansdale, PA (US); Marcela Nefliu, Schwenksville, PA (US); Gerard R. Klinzing, Wilmington, DE (US); Jie Ren, Chalfont, PA (US); Matthew Lamm, Morristown, NJ (US)

(73) Assignee: MERCK SHARP & DOHME CORP., Rahway, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/791,398

(22) Filed: Feb. 14, 2020

(65) Prior Publication Data
US 2020/0179291 A1    Jun. 11, 2020

Related U.S. Application Data

(63) Continuation of application No. 15/780,142, filed as application No. PCT/US2016/063894 on Nov. 29, 2016, now Pat. No. 10,603,282.

(60) Provisional application No. 62/261,953, filed on Dec. 2, 2015.

(51) Int. Cl.
| | | |
|---|---|---|
| *A61K 9/24* | (2006.01) | |
| *A61K 9/20* | (2006.01) | |
| *A61K 31/4439* | (2006.01) | |
| *A61K 31/675* | (2006.01) | |
| *A61K 31/7068* | (2006.01) | |
| *A61K 31/513* | (2006.01) | |
| *A61K 31/4412* | (2006.01) | |
| *A61K 9/14* | (2006.01) | |
| *A61K 31/683* | (2006.01) | |
| *A61K 9/16* | (2006.01) | |

(52) U.S. Cl.
CPC .............. *A61K 9/209* (2013.01); *A61K 9/146* (2013.01); *A61K 9/2013* (2013.01); *A61K 9/2018* (2013.01); *A61K 9/2054* (2013.01); *A61K 31/4412* (2013.01); *A61K 31/4439* (2013.01); *A61K 31/513* (2013.01); *A61K 31/675* (2013.01); *A61K 31/683* (2013.01); *A61K 31/7068* (2013.01); *A61K 9/1652* (2013.01)

(58) Field of Classification Search
CPC ...................................................... A61K 9/209
See application file for complete search history.

(56) References Cited

U.S. PATENT DOCUMENTS

| | | | |
|---|---|---|---|
| 5,047,407 A | 9/1991 | Belleau et al. | |
| 5,922,695 A | 7/1999 | Arimilli et al. | |
| 10,603,282 B2 * | 3/2020 | Panmai | A61K 2300/00 |
| 2008/0317852 A1 | 12/2008 | Lulla et al. | |
| 2014/0193491 A1 | 7/2014 | Malhotra et al. | |
| 2014/0234415 A1 | 8/2014 | McDermott et al. | |

FOREIGN PATENT DOCUMENTS

| | | |
|---|---|---|
| CN | 102573803 A | 7/2012 |
| WO | 2009106960 A2 | 9/2009 |
| WO | 2011029909 A1 | 3/2011 |
| WO | 2011120133 A1 | 10/2011 |
| WO | 2015077273 A1 | 5/2015 |
| WO | 2015179448 A1 | 11/2015 |

OTHER PUBLICATIONS

Alan McCord, IAS2015: New NNRTI doravirine as effective as efavirenz in people new to HIV treatment in early study, IAS 2015 Conference, 2015, 1.
Barnhart et al., ARVs: The Next Generation. Going Boldly Together to New Frontiers of HIV Treatement, Global Health: Science and Practice, 2015, pp. 1-11, 3.
Search Report and Written Opinion for PCT/US2016/063894, dated Feb. 21, 2017, 9 pages.
U.S. Appl. No. 15/780,142, filed May 30, 2018.

* cited by examiner

*Primary Examiner* — Brian J Davis
(74) *Attorney, Agent, or Firm* — Nicole M. Beeler; John C. Todaro

(57) ABSTRACT

The instant invention relates to pharmaceutical compositions comprising doravirine, tenofovir disoproxil fumarate and lamivudine. These compositions are useful for the treatment of HIV infection. Also disclosed are processes for making said pharmaceutical compositions.

11 Claims, No Drawings

PHARMACEUTICAL COMPOSITIONS CONTAINING DORAVIRINE, TENOFOVIR DISOPROXIL FUMARATE AND LAMIVUDINE

CROSS-REFERENCE TO RELATED APPLICATIONS

This application is a continuation application of U.S. Ser. No. 15/780,142, filed May 30, 2018, which is a national stage application under 35 U.S.C. 371 of International Patent Application No. PCT/US2016/063894, filed Nov. 29, 2016, which claims priority to U.S. Provisional Application No. 62/261,953, filed Dec. 2, 2015. Each of the aforementioned US, PCT and priority applications is incorporated by reference in its entirety.

BACKGROUND OF THE INVENTION

This invention relates to pharmaceutical compositions comprising doravirine, tenofovir disoproxil fumarate and lamivudine. These compositions are useful for the treatment of human immunodeficiency virus (HIV) infection.

Specifically, this invention relates to single tablet fixed-dose combinations of doravirine, lamivudine and tenofovir disoproxil fumarate. A fixed-dose combination is desired and useful for the treatment of HIV infection from both compliance and convenience standpoints.

The novel pharmaceutical compositions of the instant invention address the need for incorporation of high doses of doravirine, lamivudine and tenofovir disoproxil fumarate into a compact, single-unit dosage form while still maintaining comparable bioperformance to those of co-dosed doravirine, lamivudine and tenofovir disoproxil fumarate single entity formulations.

SUMMARY OF THE INVENTION

The instant invention relates to pharmaceutical compositions comprising doravirine, tenofovir disoproxil fumarate and lamivudine. These compositions are useful for the treatment of HIV infection. Also disclosed are processes for making said pharmaceutical compositions.

DETAILED DESCRIPTION OF THE INVENTION

The pharmaceutical compositions of the present invention are useful in the treatment of HIV infection. The novel pharmaceutical compositions of the instant invention address the need for incorporation of high doses of doravirine, lamivudine and tenofovir disoproxil fumarate into a compact, single-unit dosage form while still maintaining comparable bioperformance to co-dosed single entities of doravirine, lamivudine and tenofovir disoproxil fumarate.

An embodiment of the instant invention comprises a bilayer tablet that incorporates high loading of an amorphous dispersion formulation of doravirine in one layer and high loadings of crystalline formulations of lamivudine and tenofovir disoproxil fumarate in a separate layer. The resulting bilayer tablets are compact, single-unit dosage forms that have bioperformance comparable to those of individually co-dosed doravirine, lamivudine and tenofovir disoproxil fumarate.

Doravirine is an HIV reverse transcriptase (RT) inhibitor having the chemical name 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile and the following chemical structure:

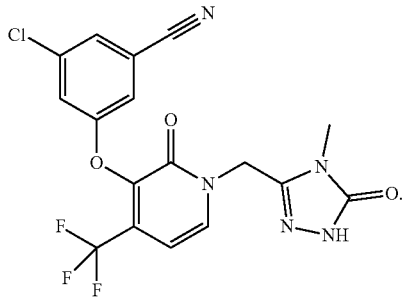 [SMILES: Cn1c(Cn2ccc(C(F)(F)F)c(Oc3cc(Cl)cc(C#N)c3)c2=O)n[nH]c1=O]

Production and the ability of doravirine to inhibit HIV reverse transcriptase is illustrated in WO 2011/120133 A1, published on Oct. 6, 2011, and U.S. Pat. No. 8,486,975, granted Jul. 16, 2013, both of which are hereby incorporated by reference in their entirety.

Tenofovir disoproxil fumarate (which can be abbreviated as "TDF") is an antiretroviral medication used to prevent and treat HIV/AIDS. It is of the nucleoside analog reverse transcriptase inhibitor (NRTI) class and is marketed under the tradename VIREAD®. TDF is disclosed in U.S. Pat. No. 5,922,695.

Lamivudine (2',3'-dideoxy-3'-thiacytidine, commonly called 3TC) is an antiretroviral medication used to prevent and treat HIV/AIDS. It is of the nucleoside analog reverse transcriptase inhibitor (NRTI) class and is marketed under the tradename EPIVIR®. Lamivudine is also abbreviated as "LAM." Lamivudine and method of treating HIV using lamivudine are disclosed in U.S. Pat. No. 5,047,407.

Doravirine is known to exist in three crystalline anhydrous forms, designated as Form I, Form II and Form III, and in an amorphous form. An amorphous dispersion formulation of doravirine can be made by spray-drying doravirine with a polymer, such as hydroxypropyl methyl cellulose acetate succinate (HPMCAS, also known as "hypromellose acetate succinate"), hydroxypropyl methyl cellulose phthalate, cellulose acetate phthalate, cellulose acetate trimellitate, methyl cellulose acetate phthalate, hydroxypropyl cellulose acetate phthalate, cellulose acetate terephthalate, cellulose acetate isophthalate, polyvinylpyrrolidinone or polyvinylpyrrolidinone-polyvinylacetate copolymers. In a class of the invention, the amorphous dispersion formulation of doravirine is made by spray-drying doravirine with hydroxypropyl methyl cellulose acetate succinate (HPMCAS-L), which significantly improves the bioavailability of doravirine.

However, the resulting amorphous dispersion formulation of doravirine poses many unique challenges, including physical stability, since doravirine is a strong crystallizer. Doravirine was found to crystallize readily in the absence of a polymer and to have a high melting point of 286° C. (see, PCT International Publication WO 2015/077273, which is hereby incorporated by reference in its entirety). Neat amorphous doravirine generated by spray-drying crystallizes within 2 weeks when stored in an open container at 5° C./ambient relative humidity (RH), 30° C./65% RH, 40° C./75% RH, and 60° C./ambient RH. For spray-dried dispersions of doravirine and HPMCAS, crystallization was observed at 35% drug loading after 16 weeks of storage and at 40% drug loading after 8 weeks of storage at 40° C./75%

RH (open). Other factors can affect physical stability, including inherent tendency of the drug to crystallize, drug loading in the dispersion, type of polymers used, hygroscopicity of the formulation and other factors.

In addition to challenges associated with physical stability, dissolution of the amorphous dispersion of doravirine is a concern due to a kinetic supersaturation effect. The composition comprising the amorphous dispersion of doravirine (doravirine and a polymer) provides a higher maximum aqueous concentration of doravirine relative to a control composition having the same concentration of doravirine but without the polymer. This supersaturation effect is transient and relies on rapid dissolution of the drug from the tablet.

Furthermore, there are processing issues due to atypical compaction properties associated with the amorphous dispersion of doravirine. The compactability of doravirine spray dried dispersion is directly correlated to the bulk density of the dispersion. Higher bulk density leads to lower tensile strength tablets. Also, recompactability of the spray dried dispersion formulations, post roller compaction is also a concern. A relatively high roller compaction force results in lower final compactability. In certain cases, tablets of formulations containing doravirine spray dried dispersions with high bulk density show failure upon compression, due to low tensile strength (see, PCT International Publication WO2015/077273).

What is needed is a formulation that can consistently deliver high doses of doravirine without encountering the observed issues related to physical stability, kinetic supersaturation effect and processing.

The pharmaceutical compositions of the present invention, which are bilayer tablets, comprise an amorphous dispersion formulation of doravirine in the first layer, and lamivudine and tenofovir disoproxil fumarate in the second layer.

In an embodiment of the invention, the first layer comprises an amorphous dispersion formulation of doravirine, a glidant, a diluent, a disintegrant and lubricants. In a class of the invention, the first layer comprises from about 25% to 75% by weight of an amorphous dispersion formulation of doravirine, and from about 25% to 75% by weight of excipients comprising glidant, diluents, disintegrants and lubricants. In a subclass of the invention, the first layer comprises from about 50% to 65% by weight of an amorphous dispersion formulation of doravirine, about 24% to 46% by weight of diluents, and about 0.1% to 1% by weight of glidants, about 4% to 8% by weight of disintegrants, about 0.25% to 2% by weight of lubricants.

In an embodiment of the invention, the second layer comprises lamivudine, tenofovir disoproxil fumarate, a glidant, a diluent, a disintegrant, and lubricants. In a class of the invention, the second layer comprises from about 15% to 45% by weight of lamivudine, from about 15% to 45% by weight of tenofovir disoproxil fumarate, and from about 10% to 70% by weight of excipients comprising glidant, diluents, disintegrants and lubricants. In a subclass of the invention, the first layer comprises from about 30% to 40% by weight of lamivudine, from about 30% to 40% by weight of tenofovir disoproxil fumarate, about 0.1% to 2% by weight of glidants, about 6% to 38% by weight of diluents, about 2% to 8% by weight of disintegrants, about 0.25% to 4% by weight of lubricants.

Optionally, the pharmaceutical compositions are film coated. The pharmaceutical compositions of the instant invention may also comprise a polishing aid such as carnauba wax, that among other uses, aids handling of the final product.

The pharmaceutical compositions of the present invention may contain one or more additional formulation ingredients that may be selected from a wide variety of excipients known in the pharmaceutical formulation art. According to the desired properties of the compositions, any number of ingredients may be selected, alone or in combination, based upon their known uses in preparing tablet compositions. Such ingredients include, but are not limited to, diluents, binders, compression aids, disintegrants, lubricants, glidants, stabilizers (such as dessicating amorphous silica), flavors, flavor enhancers, sweeteners, preservatives, colorants and coatings.

In an embodiment of the invention, the glidant, or flow aid, is colloidal silica, silicone dioxide, talc or starch. In a class of the invention, the glidant is colloidal silica.

In an embodiment of the invention, the diluents are selected from the group consisting of lactose, lactose anhydrous, lactose monohydrate, mannitol, microcrystalline cellulose, calcium phosphate, calcium phosphate dibasic, calcium carbonate and magnesium carbonate. In a class of the embodiment, the diluents are lactose monohydrate and microcrystalline cellulose.

In an embodiment of the invention the disintegrant is croscarmellose sodium, starch, crospovidone, sodium starch glycolate or any mixtures thereof. In a class of the embodiment, the disintegrant is croscarmellose sodium.

In an embodiment of the invention, the lubricant is magnesium stearate, stearic acid or sodium stearyl fumarate. In a class of the embodiment, the lubricants used are magnesium stearate and sodium stearyl fumarate, stearic acid or mixtures thereof.

In an embodiment of the invention, the pharmaceutical composition has a film coat. In a class of the invention, the film coating is an aqueous film coating. In a subclass of the invention, the film coating comprises hydroxypropylmethylcellulose, such as Opadry® II. Opadry® II, which is available from Colorcon, Inc., Harleysville, Pa., contains hydroxypropyl methyl cellulose (also known as "HPMC" or "hypromellose"), titanium dioxide, lactose monohydrate, triacetin and iron oxide yellow.

In an embodiment of the invention, the pharmaceutical composition has a polishing aid. In a class of the invention, the polishing aid is carnauba wax.

In an embodiment of the invention, the first layer comprises a glidant that is colloidal silica; a diluent that is microcrystalline cellulose; a disintegrant that is croscarmellose sodium; and a lubricant that is magnesium stearate.

In an embodiment of the invention, the second layer comprises a glidant that is colloidal silica; a diluent that is microcrystalline cellulose; a disintegrant that is croscarmellose sodium; and lubricants that are magnesium stearate and sodium stearyl fumarate.

The term "tablet" as used herein is intended to encompass compressed pharmaceutical dosage formulations of all shapes and sizes, whether uncoated or coated. Substances which may be used for coating include hydroxypropylmethylcellulose, hydroxypropylcellulose, titanium dioxide, talc, sweeteners and colorants.

The novel pharmaceutical compositions of the instant invention address the need for incorporation of high doses of doravirine, lamivudine and tenofovir disoproxil fumarate into a compact, single-unit dosage form while still maintaining comparable bioperformance to formulations of individually co-dosed doravirine, lamivudine and tenofovir disoproxil fumarate.

Initial efforts to simply combine the three active ingredients into a homogeneous composition were unsuccessful. At first, the amorphous dispersion formulation of doravirine, lamivudine and tenofovir disoproxil fumarate were roller-compacted as a single granulation and compressed into a monolithic tablet of ≤1.6 grams. However, the tablet disintegration time was very long (more than 30 min), and the in-vitro dissolution was poor. Subsequent attempts were made to prepare separate granulations for the amorphous dispersion of doravirine and for lamivudine and tenofovir disoproxil fumarate and compress the combined granulations into a monolithic tablet of ≤1.6 grams. These attempts also resulted in relatively slow tablet disintegration and slow dissolution of doravirine.

In an effort to improve the in vitro and in vivo performance of the doravirine formulation, a bilayer configuration wherein the dissolution of the doravirine moiety is not impeded by the tenofovir/lamivudine formulations was developed. Historically, a bilayer tablet configuration has been utilized to formulate active agents with physical or chemical incompatabilities resulting in degradation of interactions such as those which slow down dissolution and lower bioperformance. Doravirine is a low solubility compound classified as a class II compound based on the biopharmaceutics classification system. Hence, it is critical that the release of the active from the fixed dose combination mimics the release from the single entity formulation to ensure comparable efficacy. For the soluble actives, tenofovir disoproxil fumarate and lamivudine, co-granulating the two actives results in an eroding layer which is mechanistically different from the single entities which release the drug through layer disintegration. Separating the lamivudine and tenofovir by incorporating lamivudine in the doravirine (first) layer speeds up release of both lamivudine and tenofovir disoproxil fumarate, but considerably slows down doravirine release. Hence, achieving comparable exposure from the fixed dose combination for these actives is challenging, and the configuration in which these three moieties are presented to ensure similar performance to single entities was previously unknown The tablets of the instant invention incorporate high loading of an amorphous dispersion formulation of doravirine in one layer and high loadings of crystalline formulations of lamivudine and tenofovir disoproxil fumarate in a separate layer. It was not until the discovery of the instant invention that a physically and chemically stable tablet could be obtained that contained all three active ingredients.

Increased complexity is imparted due to the hygroscopicity of the amorphous dispersion of doravirine in one layer owing to the polymer (for example, HPMCAS), and the susceptibility to hydrolytic degradation of the crystalline tenofovir disoproxil fumarate in the other layer. The novel pharmaceutical compositions of the instant invention address the need for adequate physical and chemical stability of the tablets. Stability of the tablet, namely, chemical stability of tenofovir disoproxil fumarate and physical stability of doravirine, was ensured by controlling water ingression into and water activity in the packaging configuration. One such way is through the use of desiccants in closed containers. Another approach to ensure chemical stability of tenofovir is through physical separation between tenofovir disoproxil fumarate and lamivudine, either within the layer or the dosage form. The separation of tenofovir and lamivudine can be done either as separate layers or as separate granulations in the second layer.

In addition, the novel pharmaceutical compositions of the instant invention address the need for process robustness upon scale up. The first layer containing doravirine is susceptible to capping and interfacial crack issues during bilayer compression as well as decapping and assay loss during processing. While interfacial cracking of bilayer tablets due to low interfacial strength or differential swelling at high temperature and relative humidity is well known, bilayer cracking due to deaeration issues of the amorphous dispersion in the first layer was not known. The low bulk density of the amorphous dispersion formulation, designed to address loss on recompaction and ensure acceptable interfacial strength between the two layers, is a key factor. Deaeration based cracking was also not seen for the single entity formulation and is exacerbated for the large bilayer image. In some cases, these cracks may not be initially present on the exterior of the tablet and hence may not be visible to the naked eye but under conditions of stress such as heat and shear in a coating pan, the cracks can propagate towards the exterior and present themselves to the naked eye. A complex interplay of roller compaction pressure, tamp force and tamp positioning optimization during bilayer compression was critical to resolving the bilayer cracking. The second layer of lamivudine and tenofovir disoproxil fumarate is prone to roll sticking during roller compaction due to the high drug loadings and the inherent sticking propensity of tenofovir. The second layer formulation is also prone to extrusion during roller compaction due to the low glass transition temperature of tenofovir. Mitigation of roll sticking and extrusion required optimal selection of lubricant systems and control of process temperature. The second layer formulation is also susceptible to layer edge chipping during film coating, due to the low tensile strength of the second layer. Edge chipping was circumvented through appropriate selection of film coating systems and optimization of coating process parameters.

Co-granulating tenofovir disoproxil fumarate and lamivudine results in an eroding layer which is mechanistically different from the formulations of the single entities, which release each drug through layer disintegration. It was not known if the mechanistically different dissolution behaviors would have an impact on bioperformance. Furthermore, in the combined tablet, it was unknown whether there would be an interaction between lamivudine and tenofovir disoproxil fumarate, which could result in chemical instability of tenofovir disoproxil fumarate.

The instant invention also addresses the chemical instability of tenofovir disoproxil fumarate, which hydrolyses to form a metabolite, tenofovir mono-POC (also known as "tenofovir monoisoproxil"). The tenofovir disoproxil fumarate stability issue is exacerbated under higher temperature and humidity conditions. These higher temperature and humidity conditions can be found in Zone III (hot, dry climate, 30° C./35% RH)/Zone IV (hot, humid climate, 30° C./75% RH) countries, which include countries in South America (Brazil), sub-Saharan Africa, South Asia (India), and Southeast Asia. Some of these geographical regions coincidentally also happen to be areas where the HIV disease is most prevalent thereby making it imperative for the product to be stable in these hot and humid regions.

The pharmaceutical compositions of the instant invention are stable at temperatures up to 25° C. and up to 60% relative humidity for at least 36 months. The pharmaceutical compositions of the instant invention are stable at temperatures up to 30° C. and up to 65% relative humidity for at least 24 months. Optionally, the packaging storage can include the use of desiccants to further enhance the stability at high relative humidity.

The instant invention also addresses the need for fixed dose pharmaceutical compositions containing doravirine, lamivudine and tenofovir disoproxil fumarate. A compact single-unit dosage form with an image size no larger than 1.6 grams was developed, comprising 100 mg of doravirine (equivalent to 500 mg of doravirine spray dried intermediate), 300 mg of lamivudine and 300 mg of tenofovir disoproxil fumarate. Also, a compact dosage form for two-unit administration (taking two tablets at a time) with an image size no larger than 1.0 grams was developed, comprising 50 mg of doravirine (equivalent to 250 mg of doravirine spray dried intermediate), 150 mg of lamivudine and 150 mg of tenofovir disoproxil fumarate.

In another embodiment, the second layer can also contain lamivudine and tenofovir disoproxil fumarate which were separately granulated. As can be seen in Example 7, lamivudine and tenofovir disoproxil fumarate were granulated separately by roller compaction. In Example 8, lamivudine and tenofovir disoproxil fumarate were granulated separately by wet granulation. Probe stability data indicated that the separate granulation approaches can improve the stability profile by reducing the rate of tenofovir mono-POC (also called "mono-POC") formation, as shown in Example 9 (accelerated study at 60° C./ambient, 3 weeks).

The following examples are given for the purpose of illustrating the present invention and shall not be construed as being limitations on the scope of the invention.

EXAMPLE 1

50 MG DORAVIRINE/150 MG LAMIVUDINE/150 MG TENOFOVIR DISOPROXIL FUMARATE BILAYER TABLETS

| Components | Function | Amount [mg] | Percentage in Each Layer |
|---|---|---|---|
| Layer 1 | | | |
| Intragranular | | | |
| Doravirine[1] | Active | 50.00 | 10.0% |
| Hypromellose acetate succinate - LG (HPMC-ASLG)[1] | Polymer | 200.0 | 40.0% |
| Acetone[2] | Solvent | — | |
| Water, Purified[2] | Solvent | — | |
| Microcrystalline Cellulose | Diluent | 107.5 | 21.5% |
| Lactose Monohydrate | Diluent | 107.5 | 21.5% |
| Croscarmellose Sodium | Disintegrant | 15.00 | 3.0% |
| Colloidal Silica | Glidant | 2.50 | 0.50% |
| Magnesium Stearate | Lubricant | 1.25 | 0.25% |
| Extragranular | | | |
| Croscarmellose Sodium | Disintegrant | 15.00 | 3.0% |
| Magnesium Stearate | Lubricant | 1.25 | 0.25% |
| Layer 1 Weight | | 500.0 | 100.0% |
| Layer 2 | | | |
| Intragranular | | | |
| Lamivudine | Active | 150.0 | 30.0% |
| Tenofovir Disoproxil Fumarate | Active | 150.0 | 30.0% |
| Microcrystalline Cellulose | Diluent | 120.0 | 24.0% |
| Lactose Monohydrate | Diluent | 55.0 | 11.0% |
| Croscarmellose Sodium | Disintegrant | 10.00 | 2.0% |
| Magnesium Stearate | Lubricant | 1.25 | 0.25% |
| Extragranular | | | |
| Croscarmellose Sodium | Disintegrant | 10.00 | 2.0% |
| Magnesium Stearate | Lubricant | 3.75 | 0.75% |
| Layer 2 Weight | | 500.0 | 100.0% |
| Core Tablet Weight | | 1000.0 | |
| Opadry II 39K Film Coat | Film Coat | 25.00 | |
| Water, Purified[2] | Solvent | — | |
| Film-Coated Tablet Weight | | 1025.0 | |

[1]Prepared as spray dried intermediate
[2]Removed during processing

Doravirine layer granulation. Doravirine spray dried intermediate (see, PCT International Publication WO2015/077273), microcrystalline cellulose, lactose monohydrate, colloidal silica (sieved thru 30 Mesh with microcrystalline cellulose) and croscarmellose sodium were blended in V-blender at 25 rpm for 10 min. Magnesium stearate was sieved through 60 Mesh and added to the blender, which was blended at 25 rpm for additional 5 min. The lubricated blend was roller-compacted using the Alexanderwerk WP-120 at the following settings: 40 mm knurled roll, 37 bars, 2.0 mm gap, 1.6 mm/0.8 mm CONIDUR screens. Then, croscarmellose sodium was added to V-blender and blended at 25 rpm for 5 min. Finally, magnesium stearate was sieved through 60 Mesh and added to the blender, which was blended at 25 rpm for additional 5 min.

LAM/TDF blending and roller compaction. TDF, lamivudine, microcrystalline cellulose, lactose monohydrate, croscarmellose sodium were sieved through 30 Mesh and blended in V-blender at 25 rpm for 10 min. Magnesium stearate was sieved through 60 Mesh and added to the blender, which was blended at 25 rpm for additional 5 min. The lubricated blend was roller-compacted using the Alexanderwerk WP-120 at the following settings: 40 mm knurled roll, 55 bars, 2.0 mm gap, 1.6 mm/0.8 mm CONIDUR screens. Then, croscarmellose sodium was added to V-blender and blended at 25 rpm for 5 min. Finally, magnesium stearate was sieved through 60 Mesh and added to the blender, which was blended at 25 rpm for additional 5 min.

Bilayer Compression. Doravirine lubricated granules (layer 1) and LAM/TDF lubricated granules (layer 2) were compressed into bilayer tablets on the Piccola press using the following parameters (oval tooling, 0.708"×0.354", 500 mg layer 1 fill weight, 500 mg layer 2 fill weight, 20 kp hardness, 7.3 mm thickness, 1.7 kN tamping force, 18 kN main compression force, 10 rpm turret speed).

Film Coating. An aqueous suspension of Opadry 39K, 15% by weight, was prepared. The compressed tablets were film-coated in the O'Hara (19" pan) using the following parameters (2.5 kg tablet load, exhaust temp=45° C., air flow=400 ft$^3$/min, pan speed=10 rpm, spray rate=10 g/min).

EXAMPLE 2

100 MG DORAVIRINE/300 MG LAMIVUDINE/300 MG TENOFOVIR DISOPROXIL FUMARATE BILAYER TABLETS

| Components | Function | Amount [mg] | Percentage in Each Layer |
|---|---|---|---|
| Layer 1 | | | |
| Intragranular | | | |
| Doravirine[1] | Active | 100.0 | 12.8% |
| Hypromellose acetate succinate - LG (HPMC-ASLG)[1] | Polymer | 400.0 | 51.3% |
| Acetone[2] | Solvent | — | |
| Water, Purified[2] | Solvent | — | |
| Microcrystalline Cellulose | Diluent | 224.0 | 28.7% |
| Croscarmellose Sodium | Disintegrant | 24.0 | 3.1% |
| Colloidal Silica | Glidant | 4.00 | 0.51% |
| Magnesium Stearate | Lubricant | 2.00 | 0.26% |
| Extragranular | | | |
| Croscarmellose Sodium | Disintegrant | 24.00 | 3.1% |
| Magnesium Stearate | Lubricant | 2.00 | 0.26% |
| Layer 1 Weight | | 780.0 | 100% |
| Layer 2 | | | |
| Intragranular | | | |
| Lamivudine | Active | 300.0 | 38.5% |
| Tenofovir Disoproxil Fumarate | Active | 300.0 | 38.5% |
| Microcrystalline Cellulose | Diluent | 103.8 | 13.3% |
| Croscarmellose Sodium | Disintegrant | 23.4 | 3.0% |
| Colloidal Silica | Glidant | 7.80 | 1.0% |
| Magnesium Stearate | Lubricant | 7.80 | 1.0% |
| Sodium Stearyl Fumarate | Lubricant | 7.80 | 1.0% |
| Extragranular | | | |
| Croscarmellose Sodium | Disintegrant | 23.40 | 3.0% |
| Magnesium Stearate | Lubricant | 6.00 | 0.77% |
| Layer 2 Weight | | 780.0 | 100% |
| Core Tablet Weight | | 1560 | |
| Opadry II 39K Film Coat | Film Coat | 39.00 | |
| Water, Purified[2] | Solvent | — | |
| Carnauba Wax | Polishing Aid | 0.05 | |
| Film-Coated Tablet Weight | | 1599 | |

[1]Prepared as spray dried intermediate
[2]Removed during processing

Doravirine layer granulation. Doravirine spray dried intermediate, microcrystalline cellulose, colloidal silica (sieved thru 30 Mesh with microcrystalline cellulose) and croscarmellose sodium were blended in 1800-L Bohle bin at 6 rpm for 30 min. Magnesium stearate was sieved through 60 Mesh and added to the blender, which was blended at 6 rpm for 10 min. The lubricated blend was roller-compacted using the Alexanderwerk WP-200 at the following settings: 75 mm knurled roll, 5.6 kN/cm, 2.0 mm gap, 2.0 mm/1.0 mm CONIDUR screens. Then, croscarmellose sodium was added to the Bohle bin and blended at 6 rpm for 30 min. Finally, magnesium stearate was sieved through 60 Mesh and added to the blender, which was blended at 6 rpm for additional 10 min.

LAM/TDF blending and roller compaction. TDF, lamivudine, microcrystalline cellulose, colloidal silica (sieved thru 30 mesh with microcrystalline cellulose), and croscarmellose sodium were blended in 1800-L Bohle bin at 6 rpm for 30 min. Sodium stearyl fumarate and magnesium stearate was sieved through 60 Mesh and added to the blender, which was blended at 6 rpm for 10 min. The lubricated blend was roller-compacted using the Alexanderwerk WP-200 at the following settings: 75 mm knurled roll, 7.1 kN/cm, 2.0 mm gap, 2.0 mm/1.0 mm wire screens. Then, croscarmellose sodium was added to the Bohle bin and blended at 6 rpm for 30 min. Finally, magnesium stearate was sieved through 60 Mesh and added to the blender, which was blended at 6 rpm for 10 min.

Bilayer Compression. Doravirine lubricated granules (layer 1) and LAM/TDF lubricated granules (layer 2) were compressed into bilayer tablets on the Fette 3090 press (49 stations) using the following parameters (oval tooling, 0.850"×0.445", 780 mg layer 1 fill weight, 780 mg layer 2 fill weight, 23 kp hardness, 7.3 mm thickness, 5 kN tamping force, 37 kN main compression force, 10 rpm turret speed).

Film Coating. An aqueous suspension of Opadry 39K, yellow, 18% by weight, was prepared. The compressed tablets were film-coated in the Vector FC 150 L, using the following parameters (88 kg tablet load, exhaust temp=45° C., air flow=1250 m$^3$/hr, pan speed=4-5 rpm, spray rate=175-200 g/min). Carnauba wax was added to the film-coated tablets at the end.

EXAMPLE 3

100 MG DORAVIRINE/300 MG LAMIVUDINE/300 MG TENOFOVIR DISOPROXIL FUMARATE MONOLITHIC TABLETS

| Components | Function | Amount [mg] |
|---|---|---|
| Granulation 1 (695 mg) | | |
| Doravirine[1] | Active | 100.0 |
| Hypromellose acetate succinate - LG (HPMC-ASLG)[1] | Polymer | 400.0 |
| Acetone[2] | Solvent | — |
| Water, Purified[2] | Solvent | — |
| Microcrystalline Cellulose | Diluent | 100.0 |
| Lactose Monohydrate | Diluent | 50.00 |
| Croscarmellose Sodium | Disintegrant | 40.00 |
| Colloidal Silica | Glidant | 3.00 |
| Magnesium Stearate | Lubricant | 2.00 |
| Granulation 2 (700 mg) | | |
| Lamivudine | Active | 300.0 |
| Tenofovir Disoproxil Fumarate | Active | 300.0 |
| Microcrystalline Cellulose | Diluent | 50.00 |
| Lactose Monohydrate | Diluent | 25.00 |
| Croscarmellose Sodium | Disintegrant | 20.00 |
| Magnesium Stearate | Lubricant | 5.00 |
| Extragranular (165 mg) | | |
| Microcrystalline Cellulose | Diluent | 100.0 |
| Croscarmellose Sodium | Disintegrant | 60.00 |
| Magnesium Stearate | Lubricant | 5.00 |
| Core Tablet Weight | | 1560 |
| Opadry II 39K Film Coat | Film Coat | 39.00 |
| Water, Purified[2] | Solvent | — |
| Film-Coated Tablet Weight | | 1599 |

[1]Prepared as spray dried intermediate
[2]Removed during processing

Doravirine blending and roller compaction. Doravirine spray dried intermediate, microcrystalline cellulose, lactose monohydrate, colloidal silica and croscarmellose sodium were sieved through 30 Mesh and blended in V-blender at 25 rpm for 15 min. Magnesium stearate was sieved through 60 Mesh and added to the blender, which was blended at 25 rpm for additional 5 min. The lubricated blend was roller-compacted using the Alexanderwerk WP-120 at the following settings: 40 mm knurled roll, 28 bars, 2.0 mm gap, 1.6 mm/0.8 mm CONIDUR screens.

LAM/TDF blending and roller compaction. TDF, lamivudine, microcrystalline cellulose, lactose monohydrate, and croscarmellose sodium were sieved through 30 Mesh and blended in V-blender at 25 rpm for 15 min. Magnesium stearate was sieved through 60 Mesh and added to the blender, which was blended at 25 rpm for additional 5 min. The lubricated blend was roller-compacted using the Alexanderwerk WP-120 at the following settings: 40 mm knurled roll, 20 bars, 2.0 mm gap, 1.6 mm/0.8 mm CONIDUR screens.

Granulation blending and lubrication. Doravirine roller-compacted granules, LAM/TDF roller-compacted granules, microcrystalline cellulose (thru 30 Mesh), and croscarmellose sodium (thru 30 Mesh) were added to V-blender and blended at 25 rpm for 5 min. Then, magnesium stearate was sieved through 60 Mesh and added to the blender, which was blended at 25 rpm for additional 5 min.

Compression. The lubricated blends were compressed on the Piccola press using the following parameters (oval tooling, 0.745"×0.383", 1560 mg fill weight, 20 kp hardness, 9.7 mm thickness, 15 kN main compression force, 8 rpm turret speed).

Film Coating. An aqueous suspension of Opadry 39K, 15% by weight, was prepared. The compressed tablets were film-coated in the O'Hara (19" pan) using the following parameters (2.82 kg tablet load, exhaust temp=45° C., air flow=250 ft$^3$/min, pan speed=8 rpm, spray rate=30 g/min).

EXAMPLE 4

Biocomparabiliy of Bilayer Tablets (50 MG/150 MG/150 MG), Monolithic Tablets (100 MG/300 MG/300 MG) and Co-Dosings A biocomparability study was conducted to evaluate the relative bioavailability of the triple combinations of doravirine, lamivudine, and tenofovir disoproxil fumarate (two 50-mg bilayer tablets and a 100-mg monolithic tablet) compared to the bioavailability of doravirine, lamivudine, and tenofovir disoproxil fumarate co-administered as individual tablets (reference). The 50-mg bilayer formulation contained 50 mg doravirine, 150 mg lamivudine, and 150 mg tenofovir disoproxil fumarate, while the 100-mg monolithic formulation contained 100 mg doravirine, 300 mg lamivudine, and 300 mg tenofovir disoproxil fumarate. The data are summarized in the table below.

| PK Parameter | 2 × 50/150/150 Bilayer[a] | | 1 × 100/300/300 Monolithic[b] | |
|---|---|---|---|---|
| | GMR[c] | 90% CI | GMR | 90% CI |
| Doravirine | | | | |
| AUC0-∞ | 1.00 | 0.931-1.08 | 0.858 | 0.800-0.919 |
| Cmax | 0.977 | 0.893-1.07 | 0.713 | 0.652-0.781 |
| C24 hr | 1.02 | 0.926-1.12 | 0.871 | 0.817-0.929 |
| Lamivudine | | | | |
| AUC0-∞ | 1.02 | 0.975-1.07 | 1.09 | 1.05-1.12 |
| Cmax | 0.926 | 0.859-0.999 | 1.08 | 1.02-1.15 |
| TDF | | | | |
| AUC0-∞ | 0.994 | 0.946-1.04 | 0.975 | 0.923-1.03 |
| Cmax | 0.912 | 0.808-1.03 | 0.868 | 0.786-0.959 |

References: individual tablets of doravirine (100 mg), lamivudine (300 mg), TDF (300 mg)
[a]Bilayer Formulation: 2 tablets of 50 mg doravirine/150 mg lamivudine/150 mg TDF
[b]Monolithic Formulation: 1 tablet of 100 mg doravirine/300 mg lamivudine/300 mg TDF
[c]Geometric Mean Ratio The relative bioavailability of doravirine after administration of either the bilayer or monolithic formulation was comparable to the reference. The geometric mean ratios (GMR) of $AUC_{0-\infty}$, $C_{max}$ and $C_{24hr}$ of doravirine were 1.00, 0.977, and 1.02, respectively, for the bilayer tablet, indicating that bioavailability was the same as the reference. Slight decreases of 14%, 29%, and 13% were noted in $AUC_{0-\infty}$, $C_{max}$ and $C_{24hr}$ of doravirine, respectively, after administration of the monolithic tablet compared to the reference with GMRs of 0.858, 0.713, and 0.871, respectively. Doravirine was absorbed with a median $t_{max}$ of 3 hr for the bilayer tablet and 4 hr for the monolithic tablet, comparable to the $t_{max}$ of the reference (3 hr). The elimination tin of doravirine (~17-19 hr) was similar after all three treatments.

The relative bioavailability of lamivudine was similar to the reference with GMRs of $AUC_{0-\infty}$ and $C_{max}$ of 1.02 and 0.926, respectively, for the bilayer tablet, and the corresponding values for the monolithic tablet were 1.09 and 1.08, respectively. Following administration as a monolithic or bilayer tablet, elimination tin of lamivudine was not altered compared to the reference (12.5 hr, and 12.6 hr respectively, compared to 11.6 hr). Lamivudine $t_{max}$ was 2 hr for bilayer tablet and 1 hr for the monolithic tablet, similar to the $t_{max}$ of the reference (1 hr).

The relative bioavailability of tenofovir disoproxil fumarate when administered in both the bilayer and monolithic formulations was comparable to the reference. The geometric mean ratios of $AUC_{0-\infty}$ and $C_{max}$ of tenofovir disoproxil fumarate were 0.994 and 0.912, respectively, for the bilayer tablet, similar to the reference, while the values for the monolithic tablet were 0.975 and 0.868, respectively. A slight decrease (~13%) of the geometric mean $C_{max}$ was observed for the monolithic tablet vs. the reference.

The median $t_{max}$ for tenofovir disoproxil fumarate was 1 hr for both the bilayer and monolithic tablets, and was similar to the $t_{max}$ of the reference (1 hr). The elimination $t_{1/2}$ of tenofovir disoproxil fumarate was similar after administration of the bilayer tablet (18.0 hr), or monolithic tablet (17.8 hr) or as a co-administered tablet with lamivudine and tenofovir disoproxil fumarate tablets (18.1 hr).

EXAMPLE 5

Biocomparabiliy of Bilayer Tablets (100 MG/300 MG/300 MG) and Co-Dosings

A biocomparability study was conducted to evaluate the comparative bioavailability of a bilayer fixed-dose combination ("FDC") tablet comprised of 100 mg doravirine, 300 mg lamivudine, and 300 mg tenofovir disoproxil fumarate (TDF) to the bioavailability of co-administration of:

Doravirine 100 mg oral tablet from Merck Sharp & Dohme Corp., USA

Epivir® (lamivudine) 300 mg tablets from ViiV Healthcare UK Limited, United Kingdom and Viread® (tenofovir disoproxil fumarate) 245 mg tablets from Gilead Sciences International Limited, United Kingdom The FDC is a film-coated, bilayer tablet with doravirine in one layer and lamivudine and TDF in the other layer, as described herein.

| 1 × 100/300/300 Bilayer[a] vs Co-Dosings[b] | | |
|---|---|---|
| PK Parameter | GMR[c] | 90% CI |
| Doravirine | | |
| $AUC_{0-\infty}$ | 1.01 | 0.94-1.08 |
| $AUC_{0-last}$ | 1.02 | 0.95-1.09 |
| $C_{max}$ | 0.99 | 0.91-1.09 |
| $C_{24\,hr}$ | 1.02 | 0.94-1.12 |
| Lamivudine | | |
| $AUC_{0-\infty}$ | 1.04 | 1.00-1.09 |
| $AUC_{0-last}$ | 1.04 | 1.00-1.08 |
| $C_{max}$ | 1.00 | 0.91-1.09 |
| TDF | | |
| $AUC_{0-\infty}$ | 0.98 | 0.93-1.03 |
| $AUC_{0-last}$ | 0.99 | 0.94-1.04 |
| $C_{max}$ | 0.87 | 0.78-0.97 |

[a]Bilayer Formulation: 1 tablet of 100 mg doravirine/300 mg lamivudine/300 mg TDF
[b]Reference: individual tablets of DORAVIRINE (100 mg), Epivir® (300 mg), Viread® (245 mg)
[c]Geometric Mean Ratio As shown above, the pharmacokinetics of doravirine, lamivudine, and tenofovir disoproxil fumarate were generally similar when administered as a bilayer fixed-dose combination or the individual components. While tenofovir disoproxil fumarate $C_{max}$ was slightly decreased after administration of the bilayer fixed-dose combination tablet, compared to administration as Viread®, this decrease is not expected to be clinically meaningful.

EXAMPLE 6

Chemical Stability Data for Bilayer Tablets (100 MG/300 MG/300 MG)

The re-evaluation date ("RED") for the FDC (100 mg doravirine/300 mg tenofovir disoproxil fumarate/300 mg lamuvidine) film-coated bilayer tablet is 24 months (worldwide) stored at 2 to 25° C., based on 12-month probe stability data generated at 30° C./65% RH. The tablets were packaged in 120-mL high-density polyethylene ("HDPE") bottles with induction-sealed caps and 4 g or more of desiccant. Alternative packaging configurations, such as 90 mL or 100 mL HDPE bottles with at least 3 g or 4 g of desiccant, respectively, could be used. The alternative packaging configurations should provide similar, if not better humidity control compared to the primary package. The RED is the currently assigned shelf-life, based on the available data at the time, and can be extended with additional stability data from later timepoints. Hence, the eventual or achievable commercial shelf life can be and is expected to be longer than the mentioned RED. The tables below provide analysis of the assay and degradates for each of DORAVIRINE, lamivudine and TDF, after storage at various temperature/RH conditions at various time points. The mono-POC degradate in TDF is the key degradate which governs the shelf-life. The specification for mono-POC in the fixed-dose combination tablet is 3.5% wt.

| Assay/Degradates for Film-Coated Bilayer Tablet ("FCT") 100 mg/300 mg/300 mg: Doravirine | | | |
|---|---|---|---|
| Storage Condition | Timepoints (months) | Assay (% claim) | 1.28RRT (% claim) |
| 5° C./amb RH closed | 1 | 97.99 | 0.03 |
| 25° C./60% RH closed | 1 | 96.39 | 0.04 |
| 30° C./65% RH closed | 1 | 95.20 | 0.05 |
| 40° C./75% RH closed | 1 | 97.36 | 0.07 |
| 25° C./60% RH closed | 2 | 98.22 | 0.05 |
| 30° C./65% RH closed | 2 | 98.82 | 0.06 |
| 40° C./75% RH closed | 2 | 97.92 | 0.09 |
| 25° C./60% RH closed | 5 | 96.73 | 0.07 |
| 30° C./65% RH closed | 5 | 96.98 | 0.09 |
| 40° C./75% RH closed | 5 | 97.79 | 0.10 |
| 25° C./60% RH closed | 8 | 96.34 | 0.07 |
| 30° C./65% RH closed | 8 | 96.33 | 0.09 |
| 30° C./65% RH closed | 12 | 98.32 | 0.10 |

| Assay/Degradates for Film-Coated Bilayer Tablet 100 mg/300 mg/300 mg FCT: Lamivudine | | | |
|---|---|---|---|
| Storage Condition | Timepoints (months) | Assay (% claim) | 0.39RRT (% claim) |
| 5° C./amb RH closed | 1 | 100.06 | ND |
| 25° C./60% RH closed | 1 | 100.86 | ND |
| 30° C./65% RH closed | 1 | 101.03 | ND |
| 40° C./75% RH closed | 1 | 100.51 | ND |
| 25° C./60% RH closed | 2 | 100.15 | ND |
| 30° C./65% RH closed | 2 | 99.88 | ND |
| 40° C./75% RH closed | 2 | 100.49 | ND |
| 25° C./60% RH closed | 5 | 99.67 | ND |
| 30° C./65% RH closed | 5 | 100.7 | ND |
| 40° C./75% RH closed | 5 | 99.33 | 0.07 |
| 25° C./60% RH closed | 8 | 100.94 | ND |
| 30° C./65% RH closed | 8 | 98.87 | ND |
| 30° C./65% RH closed | 12 | 99.67 | ND |

| Assay/Degradates for Film-Coated Bilayer Tablet 100 mg/300 mg/300 mg FCT: TDF | | | | | | | |
|---|---|---|---|---|---|---|---|
| Storage Condition | Timepoints (months) | Assay (% claim) | Degradates (% claim) | | | | |
| | | | 0.53RRT | 0.59RRT | 0.62RRT | 0.66RRT | 0.69RRT |
| 5° C./amb RH | 1 | 102.12 | 0.58 | ND | ND | ND | ND |
| 25° C./60% R | 1 | 100.88 | 0.62 | 0.01 | ND | ND | ND |
| 30° C./65% R | 1 | 101.40 | 0.66 | 0.02 | ND | ND | ND |
| 40° C./75% R | 1 | 101.01 | 0.85 | 0.09 | ND | ND | ND |
| 25° C./60% R | 2 | 103.28 | 0.68 | 0.01 | ND | ND | ND |
| 30° C./65% R | 2 | 102.13 | 0.75 | 0.03 | ND | ND | ND |
| 40° C./75% R | 2 | 101.69 | 1.06 | 0.13 | 0.04 | ND | ND |

-continued

Assay/Degradates for Film-Coated Bilayer Tablet 100 mg/300 mg/300 mg FCT: TDF

| Storage Condition | Timepoints (months) | Assay (% claim) | Degradates (% claim) | | | | |
|---|---|---|---|---|---|---|---|
| | | | 0.53RRT | 0.59RRT | 0.62RRT | 0.66RRT | 0.69RRT |
| 25° C./60% R | 5 | 100.29 | 0.77 | 0.04 | ND | ND | ND |
| 30° C./65% R | 5 | 101.13 | 0.92 | 0.07 | ND | ND | ND |
| 40° C./75% R | 5 | 100.54 | 1.53 | 0.22 | 0.15 | 0.09 | 0.08 |
| 25° C./60% R | 8 | 101.78 | 0.84 | 0.05 | 0.04 | ND | ND |
| 30° C./65% R | 8 | 98.83 | 1.01 | 0.09 | 0.05 | 0.04 | 0.04 |
| 30° C./65% R | 12 | 100.49 | 1.20 | 0.10 | 0.05 | 0.05 | 0.06 |

(*) mono-POC is expressed as % LC by weight relative to TDF
ND: Not detected
RH: Relative Humidity
RRT: Relative Retention Time (compared to the parent drug in a column)

EXAMPLE 7

100 MG DORAVIRINE/300 MG LAMIVUDINE/300 MG TENOFOVIR DISOPROXIL FUMARATE BILAYER TABLETS

| Components | Function | Amount [mg] | Percentage in Each Layer |
|---|---|---|---|
| Layer 1 | | | |
| Intragranular | | | |
| Doravirine[1] | Active | 100.0 | 12.8% |
| Hypromellose acetate succinate - LG (HPMC-ASLG)[1] | Polymer | 400.0 | 51.3% |
| Acetone[2] | Solvent | — | |
| Water, Purified[2] | Solvent | — | |
| Microcrystalline Cellulose | Diluent | 224.0 | 28.7% |
| Croscarmellose Sodium | Disintegrant | 24.0 | 3.1% |
| Colloidal Silica | Glidant | 4.00 | 0.51% |
| Magnesium Stearate | Lubricant | 2.00 | 0.26% |
| Extragranular | | | |
| Croscarmellose Sodium | Disintegrant | 24.00 | 3.1% |
| Magnesium Stearate | Lubricant | 2.00 | 0.26% |
| Layer 1 Weight | | 780 | 100% |
| Layer 2 | | | |
| Intragranular | | | |
| Tenofovir Disoproxil Fumarate | Active | 300.0 | 38.5% |
| Microcrystalline Cellulose | Diluent | 51.93 | 6.7% |
| Croscarmellose Sodium | Disintegrant | 11.70 | 1.5% |
| Colloidal Silica | Glidant | 3.12 | 0.40% |
| Sodium Stearyl Fumarate | Lubricant | 4.50 | 0.58% |
| Magnesium Stearate | Lubricant | 4.50 | 0.58% |
| Lamivudine | Active | 300.0 | 38.5% |
| Microcrystalline Cellulose | Diluent | 55.68 | 7.1% |
| Croscarmellose Sodium | Disintegrant | 11.70 | 1.5% |
| Colloidal Silica | Glidant | 3.12 | 0.40% |
| Sodium Stearyl Fumarate | Lubricant | 2.25 | 0.29% |
| Magnesium Stearate | Lubricant | 2.25 | 0.29% |
| Extragranular | | | |
| Croscarmellose Sodium | Disintegrant | 23.40 | 3.0% |
| Magnesium Stearate | Lubricant | 6.00 | 0.77% |
| Layer 2 Weight | | 780 | 100% |
| Core Tablet Weight | | 1560 | |
| Opadry II 39K Film Coat | Film Coat | 39.00 | |
| Water, Purified[2] | Solvent | — | |
| Film-Coated Tablet Weight | | 1599 | |

[1]Prepared as spray dried intermediate
[2]Removed during processing

Doravirine layer granulation. Doravirine spray dried intermediate, microcrystalline cellulose, colloidal silica (sieved thru 34 T Mesh with microcrystalline cellulose) and croscarmellose sodium were blended in 40 L Bohle bin at 25 rpm for 10 min. Magnesium stearate was sieved through 74 T Mesh and added to the blender, which was blended at 25 rpm for 5 min. The lubricated blend was roller-compacted using the Alexanderwerk WP-120 at the following settings: 40 mm knurled roll, 33 bars, 2.0 mm gap, 2.0 mm/1.0 mm wire mesh screens. Then, croscarmellose sodium was added to Bohle bin and blended at 25 rpm for 10 min. Finally, magnesium stearate was sieved through 74 T Mesh and added to the blender, which was blended at 25 rpm for additional 5 min.

LAM/TDF layer blend. (i) LAM blending and roller compaction. Lamivudine (sieved thru 22 T Mesh), microcrystalline cellulose, colloidal silica (sieved thru 34 T Mesh with microcrystalline cellulose) and croscarmellose sodium were blended in 40 L Bohle bin at 25 rpm for 10 min. Sodium stearyl fumarate and magnesium stearate was sieved through 74 T Mesh and added to the blender, which was blended at 25 rpm for 5 min. The lubricated blend was roller-compacted using the Alexanderwerk WP-120 at the following settings: 40 mm knurled roll, 36 bars, 2.0 mm gap, 2.0 mm/1.0 mm wire screens. (ii) TDF blending and roller compaction. TDF, microcrystalline cellulose, colloidal silica (sieved thru 34 T mesh with microcrystalline cellulose), croscarmellose sodium were blended in 40 L Bohle bin at 25 rpm for 10 min. Sodium stearyl fumarate and magnesium stearate was sieved through 74 T Mesh and added to the blender, which was blended at 25 rpm for 5 min. The lubricated blend was roller-compacted using the Alexanderwerk WP-120 at the following settings: 40 mm knurled roll, 22 bars, 2.0 mm gap, 2.0 mm/1.0 mm wire screens. (iii) LAM and TDF granulations blending and lubrication. LAM granulation, TDF granulation and croscarmellose sodium were added to a Bohle bin and blended at 25 rpm for 10 min.

Finally, magnesium stearate was sieved through 60 Mesh and added to the blender, which was blended at 25 rpm for 5 min.

Bilayer Compression. Doravirine lubricated granules (layer 1) and LAM/TDF lubricated granules (layer 2) were compressed into bilayer tablets on the Fette 3090 press (14 stations) using the following parameters (oval tooling, 0.850"×0.445", 780 mg layer 1 fill weight, 780 mg layer 2 fill weight, 24 kp hardness, 5 kN tamping force, 35 kN main compression force, 10 rpm turret speed).

Film Coating. An aqueous suspension of Opadry 39K, yellow, 18% by weight, was prepared. The compressed tablets were film-coated in the Vector LCDS 2.5 L, using the following parameters (1.5 kg tablet load, exhaust temp=40° C., air flow=40 cfm, pan speed=12 rpm, spray rate=7.0 g/min).

EXAMPLE 8

100 MG DORAVIRINE/300 MG LAMIVUDINE/300 MG TENOFOVIR DISOPROXIL FUMARATE BILAYER TABLETS

| Components | Function | Amount [mg] | Percentage in Each Layer |
|---|---|---|---|
| Layer 1 | | | |
| Intragranular | | | |
| Doravirine[1] | Active | 100.0 | 12.8% |
| Hypromellose acetate succinate - LG (HPMC-ASLG)[1] | Polymer | 400.0 | 51.3% |
| Acetone[2] | Solvent | — | |
| Water, Purified[2] | Solvent | — | |
| Microcrystalline Cellulose | Diluent | 224.0 | 28.7% |
| Croscarmellose Sodium | Disintegrant | 24.0 | 3.1% |
| Colloidal Silica | Glidant | 4.00 | 0.51% |
| Magnesium Stearate | Lubricant | 2.00 | 0.26% |
| Extragranular | | | |
| Croscarmellose Sodium | Disintegrant | 24.00 | 3.1% |
| Magnesium Stearate | Lubricant | 2.00 | 0.26% |
| Layer 1 Weight | | 780 | 100% |
| Layer 2 | | | |
| Intragranular | | | |
| Tenofovir Disoproxil Fumarate | Active | 300.0 | 43.80 |
| Croscarmellose Sodium | Disintegrant | 13.19 | 1.93% |
| Hydroxypropyl-cellulose - EXF | Binder | 16.49 | 2.41% |
| Lamivudine | Active | 300.0 | 43.80% |
| Croscarmellose Sodium | Disintegrant | 13.19 | 1.93% |
| Hydroxypropyl-cellulose - EXF | Binder | 16.49 | 2.41% |
| Extragranular | | | |
| Croscarmellose Sodium | Disintegrant | 20.80 | 3.0% |
| Magnesium Stearate | Lubricant | 4.80 | 0.70% |
| Layer 2 Weight | | 685 | 100% |
| Core Tablet Weight | | 1465 | |
| Opadry II 39K Film Coat | Film Coat | 36.6 | |
| Water, Purified[2] | Solvent | — | |
| Film-Coated Tablet Weight | | 1501.6 | |

[1]Prepared as spray dried intermediate
[2]Removed during processing

Doravirine layer granulation. Doravirine spray dried intermediate, microcrystalline cellulose, colloidal silica (sieved thru 30 Mesh with microcrystalline cellulose), croscarmellose sodium were blended in 40 L Bohle bin at 25 rpm for 10 min. Magnesium stearate was sieved through 60 Mesh and added to the blender, which was blended at 25 rpm for 5 min. The lubricated blend was roller-compacted using the Alexanderwerk WP-120 at the following settings: 40 mm knurled roll, 34 bars, 2.0 mm gap, 2.0 mm/1.0 mm wire mesh screens. Then, croscarmellose sodium was added to the Bohle bin and blended at 25 rpm for 10 min. Finally, magnesium stearate was sieved through 60 Mesh and added to the blender, which was blended at 25 rpm for additional 5 min.

LAM/TDF layer blend. (i) LAM wet granulation. Lamivudine, croscarmellose sodium and hydropropyl cellulose were charged into a 10 L FIELDER blender (1.8 kg total) and blended for 1 min at impeller speed of 300 rpm. Then, the blend was wet-granulated with water as a granulation solution at the following settings: 300 rpm impeller speed, 1800 rpm chopper speed, 66 g/min solution delivery for 10 min. The wet granules were tray-dried at 35° C. The dried granules were milled using a Co-Mil with 40 G screen at 1500 rpm. (ii) TDF wet granulation. TDF, croscarmellose sodium and hydropropyl cellulose were charged into 10 L Fielder (2 kg total) and blended for 1 min at impeller speed of 300 rpm. Then, the blend was wet-granulated with water as a granulation solution at the following settings: 300 rpm impeller speed, 1800 rpm chopper speed, 100 g/min solution delivery for 10 min. The wet granules were tray-dried at 35° C. The dried granules were milled using a Co-Mil with 40 G screen at 1500 rpm. (iii) LAM and TDF granulations blending and lubrication. LAM granulation, TDF granulation, and croscarmellose sodium were added to a Bohle bin and blended at 25 rpm for 10 min. Finally, magnesium stearate was sieved through 60 Mesh and added to the blender, which was blended at 25 rpm for 5 min.

Bilayer Compression. Doravirine lubricated granules (layer 1) and LAM/TDF lubricated granules (layer 2) were compressed into bilayer tablets on the Fette 3090 press (7 stations) using the following parameters (oval tooling, 0.850"×0.445", 780 mg layer 1 fill weight, 685 mg layer 2 fill weight, 26 kp hardness, 5 kN tamping force, 25 kN main compression force, 10 rpm turret speed).

Film Coating. An aqueous suspension of Opadry 39K, yellow, 18% by weight, was prepared. The compressed tablets were film-coated in the Vector LCDS 2.5 L, using the following parameters (1.5 kg tablet load, exhaust temp=40° C., air flow=40 cfm, pan speed=12 rpm, spray rate=6.5 g/min).

EXAMPLE 9

CHEMICAL STABILITY DATA FOR BILAYER TABLETS (100 MG/300 MG/300 MG)

| | 0.53RRT mono-POC (% area) | | mono-POC Growth |
|---|---|---|---|
| Formulation Example | 5° C. | 60° C. | (% area) over 3 weeks |
| EXAMPLE 2 | 0.71 | 3.47 | 2.76 |
| EXAMPLE 7 | 0.69 | 2.31 | 1.62 |
| EXAMPLE 8 | 0.65 | 1.67 | 1.02 |

The stability of different configurations of bilayer tablets in relation to tenofovir mono-POC formation is shown above. The different configurations are described in Examples 2, 7 and 8 wherein the doravirine layer is similar but the TDF/lamivudine consisting second layer is either co-granulated or separately granulated via dry or wet granulation techniques. The stability when TDF and lamivudine are spatially separated is improved relative to that when TDF and lamivudine are co-granulated.

What is claimed is:

1. A tablet comprising a first layer comprising an amorphous dispersion formulation of doravirine, and a second layer comprising lamivudine and tenofovir disoproxil fumarate.

2. The tablet of claim 1 wherein the first layer further comprises a polymer.

3. The tablet of claim 2 wherein the polymer is selected from the group consisting of hydroxypropyl methyl cellulose acetate succinate, hydroxypropyl methyl cellulose phthalate, cellulose acetate phthalate, cellulose acetate trimellitate, methyl cellulose acetate phthalate, hydroxypropyl cellulose acetate phthalate, cellulose acetate terephthalate, cellulose acetate isophthalate, polyvinylpyrrolidinone and polyvinylpyrrolidinone-polyvinylacetate copolymers.

4. The tablet of claim 3 wherein the polymer is hydroxypropyl methyl cellulose acetate succinate.

5. The tablet of claim 1 wherein the first layer further comprises microcrystalline cellulose.

6. The tablet of claim 1 wherein the first layer further comprises croscarmellose sodium.

7. The tablet of claim 1 wherein the second layer further comprises microcrystalline cellulose.

8. The tablet of claim 1 further comprising a film coat.

9. The tablet of claim 1 comprising 50 mg of doravirine, 150 mg of lamivudine and 150 mg of tenofovir disoproxil fumarate.

10. The tablet of claim 1 comprising 100 mg of doravirine, 300 mg of lamivudine and 300 mg of tenofovir disoproxil fumarate.

11. A tablet comprising (i) a first layer comprising an amorphous dispersion formulation of doravirine, hydroxypropyl methyl cellulose acetate succinate, microcrystalline cellulose, and croscarmellose sodium, and (ii) a second layer comprising lamivudine, tenofovir disoproxil fumarate and microcrystalline cellulose.

* * * * *